(12) United States Patent
Feriani

(10) Patent No.: US 8,616,465 B2
(45) Date of Patent: Dec. 31, 2013

(54) NOZZLE BODY FOR A LIQUID DROPLET SPRAY DEVICE

(75) Inventor: Amir Feriani, Auvernier (CH)

(73) Assignee: EP Systems SA, Neuchatel (CH)

( * ) Notice: Subject to any disclaimer, the term of this patent is extended or adjusted under 35 U.S.C. 154(b) by 220 days.

(21) Appl. No.: 13/117,046

(22) Filed: May 26, 2011

(65) Prior Publication Data

US 2011/0290910 A1    Dec. 1, 2011

(30) Foreign Application Priority Data

May 28, 2010  (EP) .................................. 10164386

(51) Int. Cl.
*B05B 1/08* (2006.01)

(52) U.S. Cl.
USPC .................... 239/102.1; 239/553.3

(58) Field of Classification Search
USPC ........... 239/102.1, 102.2, 418, 421, 433, 592, 239/593, 594, 553.3
See application file for complete search history.

(56) References Cited

U.S. PATENT DOCUMENTS

| | | | |
|---|---|---|---|
| 4,085,893 A | 4/1978 | Durley, III | |
| 4,127,234 A * | 11/1978 | Busch | 239/558 |
| 5,173,274 A | 12/1992 | Owen | |
| 5,601,235 A | 2/1997 | Booker et al. | |
| 5,894,001 A | 4/1999 | Hitzler et al. | |
| 6,805,303 B2 | 10/2004 | Hess et al. | |
| 6,923,385 B2 * | 8/2005 | Koponen | 239/424 |

FOREIGN PATENT DOCUMENTS

| | | |
|---|---|---|
| EP | 1 129 741 A2 | 9/2001 |
| EP | 1 287 904 B1 | 11/2005 |

* cited by examiner

*Primary Examiner* — Davis Hwu

(74) *Attorney, Agent, or Firm* — Griffin & Szipl, P.C.

(57) ABSTRACT

A nozzle body (1) for a liquid droplet spray device is disclosed, wherein the nozzle body is arranged to receive a liquid substance from the liquid droplet spray device, wherein the nozzle body includes: (a) a substrate (2), and (b) a plurality of traversing output nozzles (4, 24, 34) formed in the substrate (2, 22, 32) for ejecting liquid as a low pressure mono-dispersive droplet spray, wherein each traversing output nozzle is arranged to receive the liquid such that the liquid may be expelled from the nozzle body by traversing the output nozzles, wherein the output nozzles (4, 24, 34) have straight and parallel side-walls that have a near vertical profile. The output nozzles are arranged in the substrate such that the density of the output nozzles increases from the center towards the edges of the substrate.

16 Claims, 3 Drawing Sheets

NOZZLE BODY FOR A LIQUID DROPLET SPRAY DEVICE

This application claims priority from European Patent Application No. 10 164 386.4, filed May 28, 2010, the entire disclosure of which is incorporated herein by reference.

FIELD OF THE INVENTION

The present invention relates to a nozzle body for a liquid droplet spray device suitable for atomising a liquid substance, such as a drug, a fragrance or other aerosolised liquids, as well as to the device itself. Such a device may be used, e.g., for perfume dispensers, for inkjet printer heads, for deposition of an array or arrays of droplets on a surface, for fuel injection devices of an engine or for administrating a nebulized drug to a patient by means of his or her respiratory system. Such an administration device, in its simplest form, is commonly called an inhaler. It may be used, e.g., for the controlled administration of drugs or for a variety of therapies using nebulized drug administration, including anaesthetics or during minimally invasive surgery. The device delivers the drug, which is in the form of a liquid substance, as a dispersion of atomised droplets. More specifically, the present invention concerns an improved liquid droplet spray device that efficiently creates and that fully expels a liquid droplet spray, as well as a method of manufacturing such liquid droplet spray device.

More specifically, the present invention pertains to a nozzle body (1) for a liquid droplet spray device, wherein the nozzle body is arranged to receive a liquid substance from the liquid droplet spray device, wherein the nozzle body includes a substrate (2), and a plurality of traversing output nozzles (4, 24, 34) formed in the substrate (2, 22, 32) for ejecting liquid as a low pressure mono-dispersive droplet spray, wherein each traversing output nozzle is arranged to receive liquid such that the liquid may be expelled from the nozzle body by traversing the output nozzles, wherein each output nozzle (4, 24, 34) has straight and parallel side-walls that have a near vertical profile. The output nozzles are arranged in the substrate such that the density of said output nozzles increases from the centre towards the edges of the substrate.

BACKGROUND OF THE INVENTION

Such liquid droplet spray devices are also sometimes called "piezoelectric spray devices," "aerosol generators," "nebulizers" and the like. They normally contain a nozzle body on a support part, in particular, a nozzle body of a liquid droplet spray device, which dispenses a liquid substance as a liquid droplet spray. They further generally consist of an ultrasound generating means, such as a piezoelectric actuator for causing the liquid to vibrate so as to be accelerated and expelled as droplets through outlet nozzles provided in the nozzle body. The device may further consist of elements such as a liquid space, a liquid feed and a fluid interface linked to a reservoir, as well as electrical connections between the ultrasound generating means and a corresponding electronic circuitry. The liquid may be, for example, an ambient fragrance, a perfume, an insecticide, an aromatherapy essence, a liquid pharmaceutical formulation, aqueous based liquids and flammable or combustible liquids.

Such nozzle bodies of a liquid droplet spray device are sometimes called "aperture plates," "nozzle arrays," "dosing aperture," "orifice plate," "vibratable membrane member," "dosing aperture arrangement," "aerosol generator," and the like. These terms are hence to be understood as being interchangeable throughout the present document.

In fact, such nozzle bodies and droplet spray devices are well known, for example see the document EP 1 129 741 in the name of the present Applicant. This document describes a liquid droplet spray device having a top substrate formed of a main body and of a nozzle body. The nozzle body contains a nozzle array of liquid droplet outlet means allowing a liquid substance contained in the liquid droplet spray device to exit the device, in this case, as a spray of droplets. A piezoelectric actuator is used to cause the liquid to undergo a vibration so as to generate the droplet spray.

It is well known to disperse fragrances and insecticides into the atmosphere by such a device to form a mist or cloud of small droplets of a liquid substance containing the fragrance or insecticide, and to eject the mist or cloud into the atmosphere in the form of minute liquid droplets. As the mist or cloud settles, the fragrance or insecticide evaporates from the droplets. Examples of devices for doing this are shown in U.S. Pat. Nos. 4,085,893, 5,173,274, 5,601,235 and 5,894,001. In general, these devices supply the liquid fragrance or insecticide to a vibrating atomization plate which, due to its vibrations, breaks up the liquid into fine droplets and ejects them upwardly in the form of a mist or a cloud. As the droplets fall back down, the fragrance or insecticide evaporates from the droplets and disperses into the atmosphere.

However, the conventional devices expel clouds of droplets where the density of the expelled cloud may be quite high, thereby resulting in droplets falling back down before being evaporated due to the fact that droplets "stick" to each other. In fact, such sticking leads to larger droplets that take longer to evaporate before falling back due to gravity.

It is, therefore, an object of the present invention to provide an innovative nozzle body and corresponding liquid droplet spray device for controlling the evaporation of the droplet cloud resulting from nebulising a liquid that overcomes the inconveniences and limitations presented by the prior art documents, and that allows it to minimise the fall back for expelled liquids.

SUMMARY OF THE INVENTION

Thus, the present invention concerns a nozzle body and liquid droplet spray device. For example, in accordance with a first embodiment of the present invention, a nozzle body (1) for a liquid droplet spray device is provided, wherein the nozzle body is arranged to receive a liquid substance from the liquid droplet spray device and to expel the liquid substance as a cloud of expelled droplets, wherein the nozzle body includes: (a) a substrate (2), and (b) a plurality of traversing output nozzles (4, 24, 34) formed in the substrate (2, 22, 32) for ejecting liquid as a low pressure mono-dispersive droplet spray, wherein each traversing output nozzle is arranged to receive the liquid such that the liquid may be expelled from the nozzle body by traversing the output nozzles, wherein the output nozzles (4, 24, 34) have straight and parallel side-walls that have a near vertical profile, characterised in that the output nozzles (4, 24, 34) are arranged in the substrate such that the density of the output nozzles increases from the centre towards the edges of the substrate so as to reduce fallback of the expelled droplets.

In accordance with a second embodiment of the present invention, the first embodiment is modified so that the output nozzles (4) are arranged in the substrate (2) such that the centrally located output nozzle traverses the substrate perpendicularly, whereas the output nozzles that are located towards the edges of the substrate are inclined at an angle α, with $0 < \alpha \leq 90°$. In accordance with a third embodiment of the present invention, the second embodiment is further modified so that the angle α decreases gradually for the output nozzles that are further removed from the center and closer to the edges of the substrate depending on the distance from the center of the substrate. In accordance with a fourth embodiment of the present invention, the first embodiment, the second embodiment, and the third embodiment are further modified so that the distance d1 between adjacent output nozzles that are located at or near the centre of the substrate is larger than the distance d2 between adjacent output nozzles that are located at or near an edge of the substrate.

In accordance with a fifth embodiment of the present invention, the first embodiment is modified so that the diameter of output nozzles that are located at or near the center of the substrate is smaller than the diameter of output nozzles that are located at or near an edge of the substrate. In accordance with a sixth embodiment of the present invention, a liquid droplet spray device (8, 7) for ejecting a liquid as a spray of droplets is provided, and it includes: (i) a housing (42), (ii) a space (44) within the housing for containing a liquid substance, (iii) means for supplying the liquid substance to the space (44), and (iv) ultrasound generating means (46) disposed to transfer ultrasound to the liquid substance in the space (44) such that the liquid undergoes vibrations, characterised in that the liquid droplet spray device further comprises a nozzle body according to anyone of the first embodiment, the second embodiment, the third embodiment, the fourth embodiment and the fifth embodiment, wherein the nozzle body is arranged in the housing.

Thanks to the features of the nozzle body and liquid droplet spray device, according to the present invention, it is possible to reliably minimise the fall back. Advantageously, in some preferred embodiments, it is additionally possible to control directivity of the expelled liquid. In fact, according to the present invention, the output nozzles of the nozzle body are arranged in such a manner that the density of cloud caused by the expelled liquid is lower in the centre of the cloud than for a conventional nozzle body, thus allowing fallback to be minimized. Advantageously, in certain embodiments, the density of cloud caused by the expelled liquid may be lower in the center of the cloud than at the peripheral part of the cloud. By having a non-uniform density of the cloud, the fallback can be further reduced.

BRIEF DESCRIPTION OF THE DRAWINGS

Other features and advantages of the method and liquid droplet spray device, according to the present invention, will become clear from reading the following description, which is given solely by way of a non-limitative example thereby referring to the attached drawings in which:

FIG. 2b is an enlarged view of FIG. 2a;

DETAILED DESCRIPTION OF THE INVENTION

Examples of different embodiments of the invention will be described as follows. In general, a nozzle body is formed of a substrate having traversing nozzles functioning as fluid passages allowing ejection of liquid as a spray of droplets. Such nozzles may be formed by etching or laser drilling or, the like, in a manner well known to a person skilled in the art. Suitable materials for the nozzle body may be, for example, silicon, plastics, or the like.

First Embodiment

Figure 1:
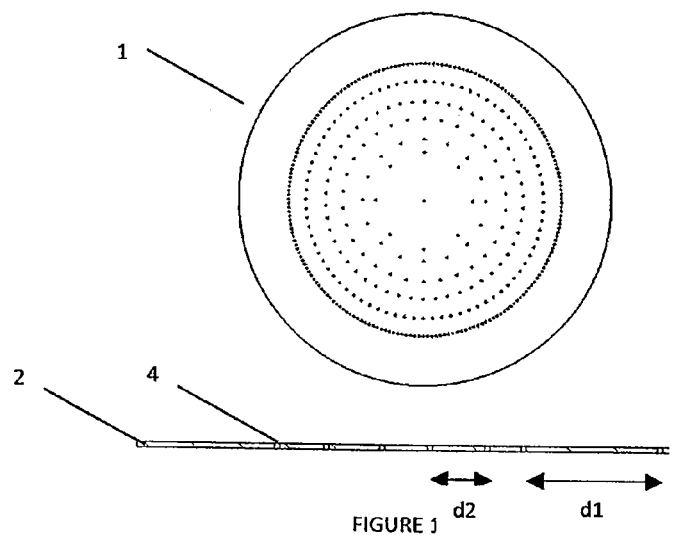
FIG. 1 shows plan and cross-sectional views of an example of a nozzle body in a first embodiment according to the present invention.

FIG. 1 shows an example of a nozzle body suitable for a liquid droplet spray device in a first embodiment according to the present invention. Nozzle body 1 is arranged to receive a liquid substance from the liquid droplet spray device in a known manner and consists of a substrate 2 provided with traversing output nozzles 4. Substrate 2 may be made of silicon or plastics or the like. The main requirement for the substrate 2 is that the material used can be pierced to obtain traversing output nozzles with straight sidewalls. A plurality of output nozzles 4 is provided as fluid passages to allow liquid to be expelled from the spray device in a manner known in the art. For example, in a manner known as such (see also FIG. 4A), a liquid chamber 44 may be provided adjacent to the nozzle body 41, and the liquid may be put into vibration by ultrasound generating means 46, such as a piezoelectric actuator, such that the ultrasound acts on the liquid forcing it through the output nozzles 4.

Each output nozzle 4 has straight and parallel sidewalls, which have a near vertical profile. According to the present invention, the plurality of output nozzles 4 is arranged in substrate 2 such that the density of the output nozzles 4 increases from the centre towards the edges of the substrate.

Thus, as shown in FIG. 1, the distance d1 between adjacent output nozzles 4 that are located at or near the centre of substrate 2 is larger than the distance d2 between adjacent output nozzles 4 that are located at or near an edge of substrate 2. Thanks to this arrangement, fewer liquid droplets are expelled from the centre of the nozzle body as compared to those that are expelled from the edges of the nozzle body. The resulting effect is that the cloud formed by the expelled droplets has a lower density in its centre than at its periphery. Because of this lower central density, as compared to conventional spray devices with a regular array arrangement of output nozzles, the probability that droplets "stick" to each other is lower thus making the cloud lighter. This leads to a reduced fallback of expelled droplets.

Indeed, the present Applicant has found that an increased density in the middle of the expelled cloud increases chances of fallback due to interference of droplets that may stick to each other. The thus formed larger droplets take longer to evaporate and may fallback to the surface from which they are expelled before full evaporation. By reducing the density in the middle of the cloud, the risk of interference is reduced because there are fewer droplets. At the periphery of the cloud, the risk of interference is in any case smaller, and droplets can evaporate easier than those located in the middle of a cloud.

Second Embodiment

Figure 2A:
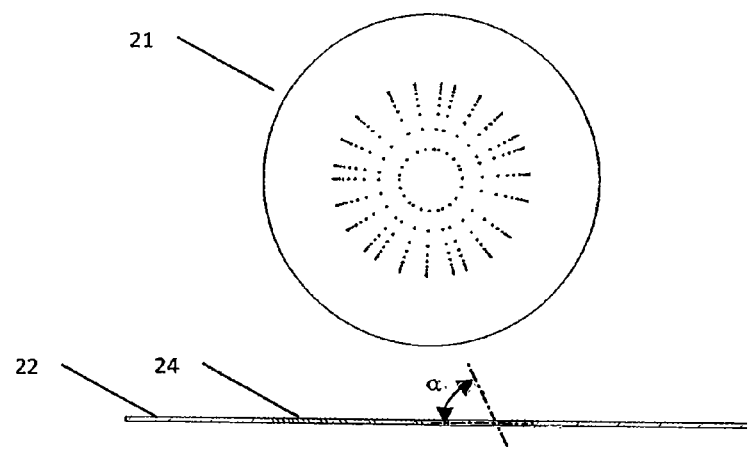
FIG. 2a shows plan and cross-sectional views of an example of a nozzle body in the second embodiment according to the present invention.

FIG. 2 shows an example of a nozzle body suitable for a liquid droplet spray device in a second embodiment according to the present invention. Nozzle body 21 of this second embodiment is similar to the nozzle body 1 of the first embodiment, except for the arrangement of the output nozzles. Similar parts and arrangements will not be described here in detail. As shown in FIG. 2a, nozzle body 21 differs from nozzle body 1 in that the output nozzles 24 located away from the centre, and towards the edges of the substrate 22, are inclined and are arranged at an angle α, where 0<α≤90°, with respect to the bottom surface of the nozzle body, i.e. that surface that is arranged to receive liquid to be expelled. The centrally arranged output nozzle, or output nozzles, are at an angle α=90° with respect to this bottom surface. The output nozzles 24 closer to the edge of the substrate 22 may be all arranged at the same angle α or may have varying angles α, where this angle α may decrease, for instance from less than 90° towards 0° when going from the centre of substrate 12 towards its edges.

Thanks to this inclination, the resulting expelled cloud has a lower density in its middle as compared to a conventional spray device with a regular array of output nozzles. Consequently, this arrangement also allows for a reduced fallback due to a reduced risk of interference of expelled droplets. Advantageously, this arrangement of the present invention allows for a certain degree of directivity of the expelled cloud by varying α of the non-centrally arranged output nozzles 24.

Figure 2B:
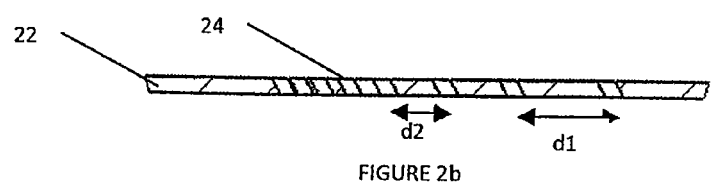

Furthermore, as shown in FIG. 2b, the distance between the output nozzles is varied in the same manner as described above for the first embodiment, i.e. the distance d1 between adjacent output nozzles 24 that are located at or near the centre of substrate 22 is larger than the distance d2 between adjacent output nozzles 24 that are located at or near an edge of substrate 22. As shown in FIG. 2a, the output nozzles 24 of the nozzle body 21 are arranged in a radial manner with respect to alignment of output nozzles located near the centre of the substrate 22 and output nozzles located at or near the edge of the substrate 22.

Third Embodiment

Figure 3:
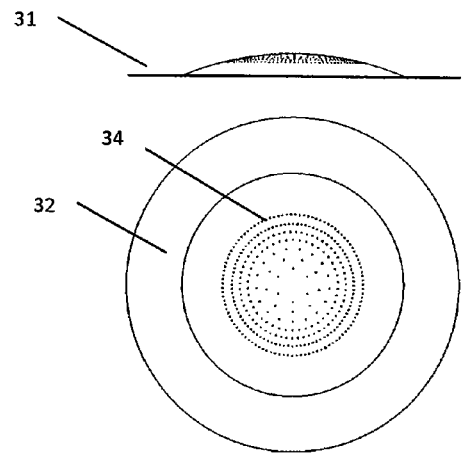
FIG. 3 shows plan and side views of an example of a nozzle body in a third embodiment according to the present invention.

FIG. 3 shows an example of a nozzle body suitable for a liquid droplet spray device in a third embodiment according to the present invention. Nozzle body 31 of this third embodiment is similar to the nozzle body of the first embodiment, except for the output nozzles and the geometry of the nozzle body. Similar parts and arrangements will not be described here in detail. Nozzle body 31 differs from nozzle body 1 in that the output nozzles 34 have varying diameters, smaller when arranged near the centre of the substrate 32 and larger when arranged towards the edges of substrate 32. Thus, the traversing nozzles 34 may have different diameters resulting in different nozzle sizes and thus in different droplet sizes being expelled.

Of course, it is also possible to arrange the nozzles such that a desired spray is obtained, for example by having a mix of different sized nozzles in the centre and towards the edges. As shown in FIG. 3, the substrate has a domed central region and a flat peripheral region. The nozzles 34 are formed in the domed central region of the substrate 32.

Figure 4A:
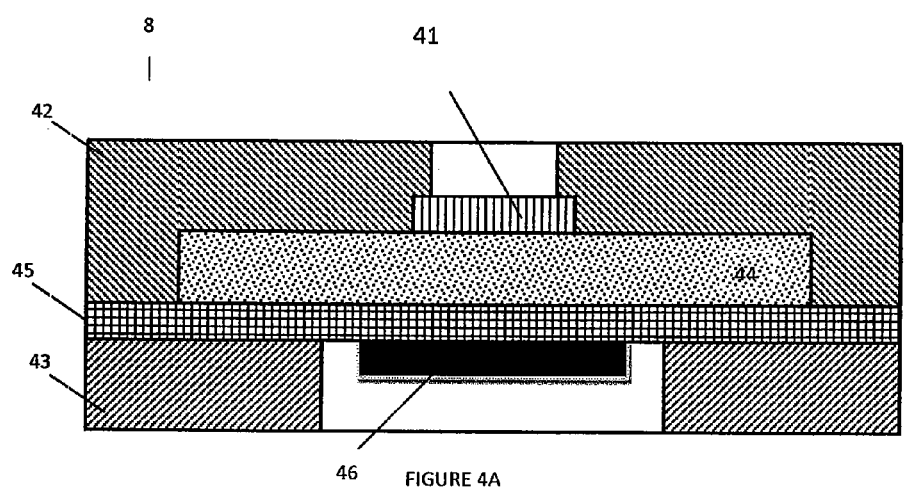
FIG. 4A shows a first example of a liquid droplet spray device including a nozzle body according to the present invention.

FIG. 4A shows a first example of a liquid droplet spray device including a nozzle body according to the present invention. Liquid droplet spray device 8 comprises, in a conventional manner, a housing 42 comprising a substrate that includes a nozzle body 41. Nozzle body 41 may be anyone of the nozzle bodies 1, 21 and 31 described in the embodiments above. A space 44, i.e. a liquid chamber, may be provided adjacent to the nozzle body 41. Ultrasound generating means 46, such as a piezoelectric actuator, may be provided on a second substrate 43 and is disposed to vibrate liquid in space 44 by the generated ultrasound such that the ultrasound acts on the liquid forcing it through the output nozzles of the nozzle body 41. Advantageously, an actuating membrane 45 may be provided between ultrasound generating means 46 and the chamber 44 to transmit the ultrasound to the liquid. Liquid feed means (not shown) may further be provided to supply liquid from a reservoir to space 44 in a manner known as such.

Figure 4B:
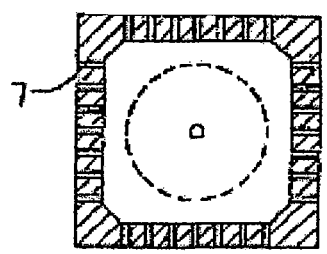
FIG. 4B shows a second example of a liquid droplet spray device including a nozzle body according to the present invention.

FIG. 4B shows a second example of a liquid droplet spray device 7 including a nozzle body according to the present invention. This device is arranged such that droplets are sprayed from the side, instead of the top of the device, in a manner similar to that disclosed in the document EP-B-1 287 904 assigned to the present Applicant (also published as U.S. Pat. No. 6,805,303 B2, which is incorporated herein by reference for all that it discloses). Here too, the nozzle body is again one as described in the embodiments above (i.e., may correspond to nozzle body 1, 21 or 31), and is arranged such that droplets are sprayed side ways. In the mentioned EP patent document, the spray device sprays in all directions, i.e. from each side of the spray device, but it is of course possible to only spray in one or several directions by spraying from one or more sides.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A nozzle body for a liquid droplet spray device, wherein the nozzle body is arranged to receive a liquid substance from the liquid droplet spray device and to expel the liquid substance as a cloud of expelled droplets, wherein the nozzle body comprises:
   (a) a substrate; and
   (b) a plurality of traversing output nozzles formed in the substrate for ejecting liquid as a low pressure monodispersive droplet spray, wherein each traversing output nozzle is arranged to receive liquid so that the liquid is expelled from the nozzle body by traversing the output nozzles, wherein the output nozzles have straight and parallel side-walls that have a near vertical profile, wherein
   a first distance between adjacent output nozzles that are located at or near a center of the substrate is larger than a second distance between adjacent output nozzles that are located at or near an edge of the substrate, and
   the output nozzles are arranged in the substrate so that density of the output nozzles increases from the center of the substrate towards the edge of the substrate so that fewer liquid droplets are expelled from the center of the nozzle body as compared to the liquid droplets that are expelled from the edge of the nozzle body.

2. A nozzle body according to claim 1, wherein said plurality of traversing output nozzles are arranged in said substrate so that a centrally located output nozzle traverses said substrate perpendicularly, whereas those output nozzles that are located towards the edges of said substrate are inclined at an angle α, wherein 0<α≤90°.

3. A nozzle body according to claim 2, wherein the angle α decreases gradually for those output nozzles that are further removed from the center of the substrate and closer to the edge of the substrate depending on a distance from the center of the substrate.

4. A liquid droplet spray device for ejecting a liquid as a spray of droplets, comprising:
   a housing;
   a space formed within the housing for containing a liquid substance;
   means for supplying said liquid substance to the space;
   ultrasound generating means disposed to transfer ultrasound to said liquid substance in the space so that said liquid substance undergoes vibrations; and
   a nozzle body according to claim 3 arranged in the housing.

5. A nozzle body according to claim 2, wherein a first distance between adjacent output nozzles that are located at or near the center of the substrate is larger than a second distance between adjacent output nozzles that are located at or near the edge of said substrate.

6. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 5 arranged in the housing.

7. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 2 arranged in the housing.

8. A nozzle body according to claim 1, wherein a diameter of those output nozzles that are located at or near the center of said substrate is smaller than a diameter of those output nozzles that are located at or near the edge of said substrate.

9. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 1 arranged in the housing.

10. A nozzle body according to claim 1, wherein a first distance between adjacent output nozzles that are located at or near the center of the substrate is larger than a second distance between adjacent output nozzles that are located at or near the edge of said substrate.

11. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 10 arranged in the housing.

12. A nozzle body for a liquid droplet spray device, wherein the nozzle body is arranged to receive a liquid substance from the liquid droplet spray device and to expel the liquid substance as a cloud of expelled droplets, wherein the nozzle body comprises:

(a) a substrate; and (b) a plurality of traversing output nozzles formed in the substrate for ejecting liquid as a low pressure monodispersive droplet spray, wherein each traversing output nozzle is arranged to receive liquid so that the liquid is expelled from the nozzle body by traversing the output nozzles, wherein the output nozzles have straight and parallel side-walls, wherein the output nozzles are arranged in the substrate so that density of the output nozzles increases from a center of the substrate towards an edge of the substrate so as to reduce fallback of expelled droplets, and the plurality of traversing output nozzles are arranged in the substrate so that a centrally located output nozzle traverses the substrate perpendicularly, whereas those output nozzles that are located towards the edges of said substrate are inclined at an angle $\alpha$, wherein $0<\alpha\leq 90°$, and wherein the angle $\alpha$ decreases gradually for those output nozzles that are further removed from the center of the substrate and closer to the edge of the substrate depending on a distance from the center of the substrate.

13. A nozzle body according to claim 12, wherein a first distance between adjacent output nozzles that are located at or near the center of the substrate is larger than a second distance between adjacent output nozzles that are located at or near the edge of said substrate.

14. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 13 arranged in the housing.

15. A nozzle body for a liquid droplet spray device, wherein the nozzle body is arranged to receive a liquid substance from the liquid droplet spray device and to expel the liquid substance as a cloud of expelled droplets, wherein the nozzle body comprises:

(a) a substrate; and (b) a plurality of traversing output nozzles formed in the substrate for ejecting liquid as a low pressure monodispersive droplet spray, wherein each traversing output nozzle is arranged to receive liquid so that the liquid is expelled from the nozzle body by traversing the output nozzles, wherein the output nozzles having straight and parallel side-walls that have a near vertical profile, wherein the output nozzles are arranged in the substrate so that density of the output nozzles increases from a center of the substrate towards an edge of the substrate so as to reduce fallback of expelled droplets, wherein a diameter of those output nozzles that are located at or near the center of the substrate is smaller than a diameter of those output nozzles that are located at or near the edge of the substrate.

16. A liquid droplet spray device for ejecting a liquid as a spray of droplets, comprising:

a housing;

a space formed within the housing for containing a liquid substance;

means for supplying said liquid substance to the space;

ultrasound generating means disposed to transfer ultrasound to said liquid substance in the space so that said liquid substance undergoes vibrations; and a nozzle body according to claim 15 arranged in the housing.

* * * * *